United States Patent
Perret et al.

(10) Patent No.: US 10,864,016 B2
(45) Date of Patent: Dec. 15, 2020

(54) DYNAMIC EXTERNAL ATTACHMENT DEVICE FOR OSTEOSYNTHESIS

(71) Applicant: GEXFIX SA, Carouge-Geneve (CH)

(72) Inventors: Jean-Pierre Perret, Thiez (FR); Filadelfio Marletta, Grancia (CH); Jan Van Aaken, Geneva (CH); Kun Liu, Beijing (CN)

(73) Assignee: GEXFIX SA

( * ) Notice: Subject to any disclaimer, the term of this patent is extended or adjusted under 35 U.S.C. 154(b) by 155 days.

(21) Appl. No.: 15/857,941

(22) PCT Filed: May 13, 2016

(86) PCT No.: PCT/EP2016/060841
§ 371 (c)(1),
(2) Date: Jun. 15, 2018

(87) PCT Pub. No.: WO2017/001106
PCT Pub. Date: Jan. 5, 2017

(65) Prior Publication Data
US 2018/0296246 A1      Oct. 18, 2018

(30) Foreign Application Priority Data
Jun. 29, 2015   (FR) ...................................... 15 56079

(51) Int. Cl.
*A61B 17/64*      (2006.01)
*A61B 17/60*      (2006.01)

(52) U.S. Cl.
CPC ...... *A61B 17/6466* (2013.01); *A61B 17/6425* (2013.01); *A61B 17/6441* (2013.01); *A61B 2017/606* (2013.01)

(58) Field of Classification Search
CPC . A61B 17/66; A61B 17/6441; A61B 17/6425; A61B 17/6491; A61B 2017/606; A61B 17/6466
See application file for complete search history.

(56) References Cited

U.S. PATENT DOCUMENTS 3,727,610 A * 4/1973 Riniker .............. A61B 17/6441
                                                    606/56
3,807,394 A * 4/1974 Attenborough ........ A61B 17/68
                                                    606/60
(Continued)

FOREIGN PATENT DOCUMENTS

EP          1 898 815          8/2013

OTHER PUBLICATIONS

International Preliminary Report oin Patentability (with English translation) dated Jan. 2, 2018 for International Application No. PCT/EP2016/060841

(Continued)

*Primary Examiner* — Ellen C Hammond
(74) *Attorney, Agent, or Firm* — Fay Sharpe LLP

(57) ABSTRACT

Pair of dynamic external fixation devices (100) for the reduction of fractures of bone fragments, said devices (100) being arranged on either side of a first bone portion traversed by a first pin (10) in a proximal position and a second bone portion traversed by a second pin (11) in distal position, while each of the dynamic external fixation devices (100) includes a first body (1) having a longitudinal axis profile (X, X'), having a proximal bore (5) passing through an axis (Y, Y') in combination with the first pin (10), said first body (1) being embedded in a first coil spring (8), while said first spring (8) is nested in a second coil spring (12), mounted in conjunction with a second body mounted in conjunction on (Continued)

said first body (1), while the second body is mounted in conjunction with the second pin (11).

19 Claims, 7 Drawing Sheets

(56) References Cited

U.S. PATENT DOCUMENTS

| | | | | |
|---|---|---|---|---|
| 4,456,004 A * | 6/1984 | Kenny | ............... | A61B 17/6441 606/57 |
| 5,074,865 A * | 12/1991 | Fahmy | ............... | A61B 17/6425 606/105 |
| 5,672,175 A * | 9/1997 | Martin | ................ | A61B 17/025 606/105 |
| 5,976,125 A | 11/1999 | Graham | | |
| 6,162,223 A * | 12/2000 | Orsak | ................ | A61B 17/6425 606/59 |
| 6,508,817 B1 * | 1/2003 | Pensler | ................ | A61B 90/02 606/57 |
| 6,730,087 B1 * | 5/2004 | Butsch | ............... | A61B 17/7216 606/105 |
| 6,796,984 B2 * | 9/2004 | Soubeiran | .......... | A61B 17/7216 606/300 |
| 9,492,199 B2 * | 11/2016 | Orsak | .................... | A61B 17/66 |
| 2003/0204190 A1 * | 10/2003 | Li | ........................ | A61B 17/663 606/90 |
| 2005/0010233 A1 * | 1/2005 | Wittenstein | ........ | A61B 17/7216 606/90 |
| 2005/0171543 A1 * | 8/2005 | Timm | ................ | A61B 17/7025 606/257 |
| 2005/0203509 A1 * | 9/2005 | Chinnaian | .......... | A61B 17/6491 606/54 |
| 2005/0261680 A1 * | 11/2005 | Draper | ............... | A61B 17/6425 606/59 |
| 2005/0288670 A1 * | 12/2005 | Panjabi | .............. | A61B 17/7007 606/257 |
| 2007/0043356 A1 * | 2/2007 | Timm | ................ | A61B 17/7007 606/279 |
| 2008/0195095 A1 * | 8/2008 | Renard | ............. | A61B 17/6491 606/54 |
| 2008/0275555 A1 * | 11/2008 | Makower | ............... | A61B 17/68 623/14.12 |
| 2012/0226277 A1 * | 9/2012 | Tan | .................... | A61B 17/6425 606/59 |
| 2014/0025075 A1 * | 1/2014 | Hokanson | .............. | A61B 17/66 606/58 |
| 2014/0336648 A1 * | 11/2014 | Van Aaken | ............ | A61B 17/66 606/58 |
| 2016/0066955 A1 * | 3/2016 | Renard | ............. | A61B 17/6491 606/54 |
| 2018/0092663 A1 * | 4/2018 | Gordon | ............. | A61B 17/6433 |
| 2018/0296246 A1 * | 10/2018 | Perret | ................ | A61B 17/6425 |

OTHER PUBLICATIONS

International Search Report (with English translation) dated Jul. 1, 2016 for International Application No. PCT/EP2016/060841.
Written Opinion (with English translation) dated Jul. 1, 2016 for International Application No. PCT/EP2016/060841.

* cited by examiner

DYNAMIC EXTERNAL ATTACHMENT DEVICE FOR OSTEOSYNTHESIS

FIELD OF INVENTION

The present invention relates to a pair of dynamic external fixation devices, for the reduction of fractures of bone fragments by osteosynthesis, in particular of osteoarticular trauma of the fingers of the hand. CL BACKGROUND The reduction and the stabilization of a digital fracture, in particular of a fracture of an end of a phalanx, are necessary in order to allow an early mobilization. Early mobilization is the best way to fight edema, joint stiffness and adhesions.

Fractures of the phalanges are common among young people, athletes, workplace accidents, and the elderly when they fall.

The available treatments are mainly of a functional, orthopedic or surgical type, such as by osteosynthesis techniques. These surgical techniques of osteosynthesis consist of the reduction and immobilization of bone fragments using screws, pins, osteosynthesis plates or external fixators.

Documents U.S. Pat. No. 5,976,125 and US 2014/0025075 disclose proximal and distal external fixators connected to the bone fragments, to be reduced by screws or pins. The proximal and distal external fixators are further connected by a threaded rod. Traction or distraction is achieved by the rotation of the threaded rod. These devices have a large size. These external fixators are not entirely satisfactory, especially for the comfort of the patient.

Document EP 1 898 815 describes elastic external fixators comprising a coil spring cooperating with two bodies, capable of reducing two portions of bone. Each of the two bodies comprises a bore capable of passing a pin connected to a portion of bone. At least one of the pins passes through the coil spring.

Document US 2014/0336648 describes a pair of external fixators comprising a rod composed of a base, comprising a bore adapted to receive a first pin, from a rod body located in the extension of the base. The rod body further comprises a lumen arranged along the longitudinal axis of the rod body. A coil spring is arranged around the rod body. A second pin, located in the lumen of the rod body, cooperates with the spring.

The modulation of the force intensity to be exerted between the two bone portions of these last two documents is achieved by the pivoting of the spring. However, a significant portion of the spring protrudes from the external fixator in the distal position. The portion of the free spring causes discomfort and discomfort in the daily life of the patient, limiting his/her freedom of movement and requiring vigilance not to snag the spring in these movements.

SUMMARY OF THE INVENTION

The present invention thus proposes dynamic external fixation devices, making it possible to overcome the aforementioned drawbacks.

Thus, the invention relates to a pair of dynamic external fixation devices, for the reduction of fractures of bone fragments, the two devices are arranged on either side of a first portion of bone traversed by a first pin in the proximal position and a second portion of bone traversed by a second pin in the distal position. Each of the dynamic external fixation devices comprises a first body portion formed from a longitudinal profile, having a first general axis of symmetry, the first body portion comprising at least one proximal bore passing therethrough along a second axis that cooperates with the first pin. The first body is inserted in a first coil spring, while the latter is inserted in a second coil spring, mounted in cooperation with a second body mounted cooperatively on the first body. The second body is mounted together with the second pin.

According to an alternative, the first body comprises a lumen arranged longitudinally along the first general axis of symmetry.

According to one embodiment, the second body is a collar in combination with and mounted at the end of the distal end of the second spring, while the distal end of the collar interacts with the second pin arranged in the lumen, oriented parallel to the second axis passing through the proximal bore of the first body.

According to another embodiment, the second body is a pivot comprising a head, comprising a distal bore interacting with the second pin, a body cooperating with the lumen oriented perpendicularly to the second axis passing through a proximal bore, and a closure element, arranged opposite to the head.

According to the previous embodiment, each of the devices according to the invention comprises a collar in combination with and mounted at the end of the distal end of the second spring, while the distal end of the collar interacts with the proximal end of the pivot.

According to another embodiment, each of the devices comprises a collar, comprising a thread complementary to the wind of the second spring, and is rotationally mounted on this latter, while the distal end of the second spring interacts with the proximal end of the pivot.

According to another alternative, the second body is a first collar, comprising a distal bore passing through, axially oriented parallel to the second axis of the proximal bore, the second pin interacting with the distal bore of the second body.

According to one embodiment, each of the devices comprises a second collar, comprising a thread complementary to the coil of the second spring, while the second collar is rotationally mounted on the second coil spring, the distal end of the second spring interacting with the proximal end of the first collar.

According to another embodiment, each of the devices comprises a second collar in combination with the distal end of the second spring, the second collar is mounted at the end of the second spring, the distal end of the second collar interacting with the proximal end of the first collar.

According to one feature, the first body includes a proximal portion, wherein is arranged at least one proximal through bore in conjunction with the first pin, a central part, and a distal portion.

According to the preceding feature, the proximal portion of the first body has a larger section than that of the central and distal part, the junction of the proximal portion and the central portion forms a shoulder serving as a compression stop for the first coil spring.

According to one embodiment, the proximal end of the first collar is engaged in a recess, arranged in line with the shoulder, while the first spring is blocked in rotation by the recess and stops against the shoulder.

According to another embodiment, the central portion is composed of two parts, namely a proximal portion of a larger section and a second part, of a less prominent section, the junction of these two parts forms a second shoulder serving as a stop for the proximal end of the second spring in the extreme distraction position.

According to another embodiment, the proximal portion of the first body has a truncated cylindrical section, namely a section comprising two parallel sides and two opposite concave shaped sides.

According to an additional feature, the diameter of the coil of the second spring is greater than that of the first spring.

BRIEF DESCRIPTION OF THE DRAWINGS

Other features and advantages of the invention will become apparent from the description which follows, with reference to the accompanying drawings which are given by way of non-limiting examples.

FIG. 1 is a perspective view of a pair of dynamic external fixation devices (100) in use.

FIG. 2 is a perspective view of a dynamic external fixation device (100).

FIG. 3 is a view from above according to (D) of FIG. 2.

FIG. 4 is a front view according to (F) of FIG. 2.

FIG. 5 is a partial view, in perspective, of the dynamic external fixing device (100), illustrating the first body (1)

FIG. 6 is a partial perspective view of the dynamic external fixation device (100) illustrating the second body.

FIG. 8 is a perspective view of a dynamic external fixation device (100) in the extreme traction position.

FIG. 9 is a perspective view of a dynamic external fixation device (100) in the extreme distraction position.

FIG. 10 is a sectional view of FIG. 8.

FIG. 11 is a perspective view of the dynamic external fixation device (100).

FIG. 12 is a perspective view of a pivot (14).

DETAILED DESCRIPTION OF THE INVENTION

Figure 1:
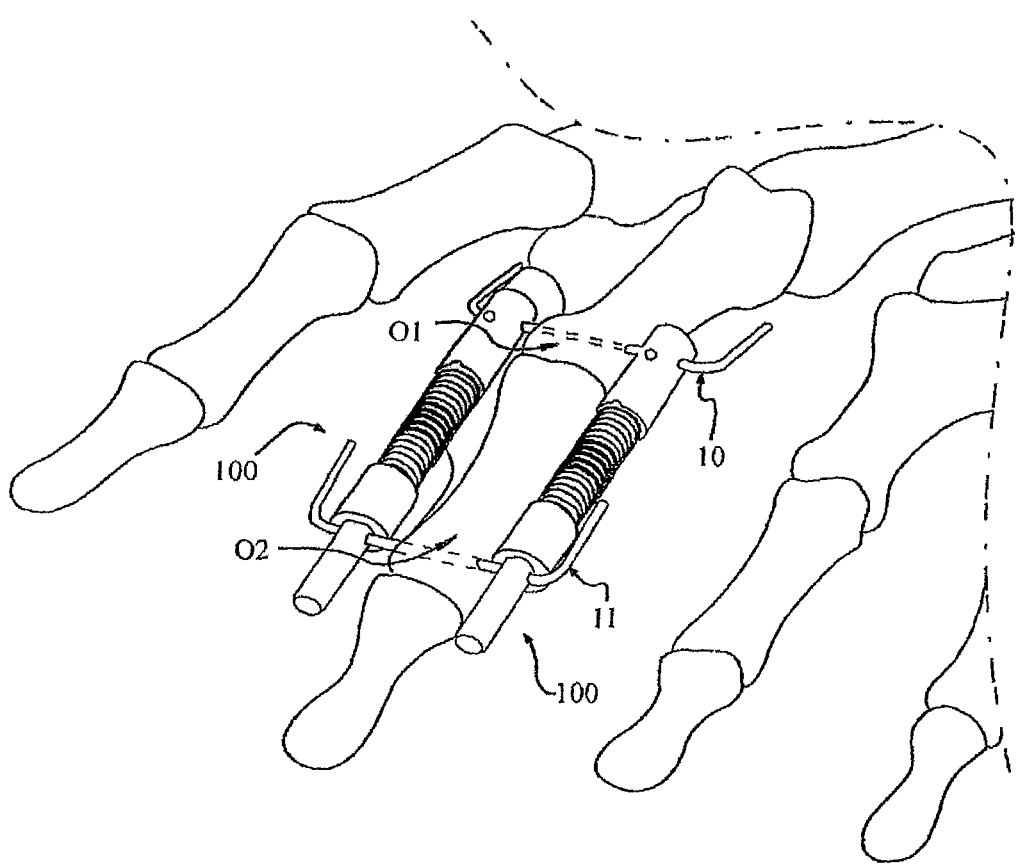
FIGS. 1 to 6 are views of the dynamic external fixation device (100), according to one embodiment of the invention.
Figure 2:
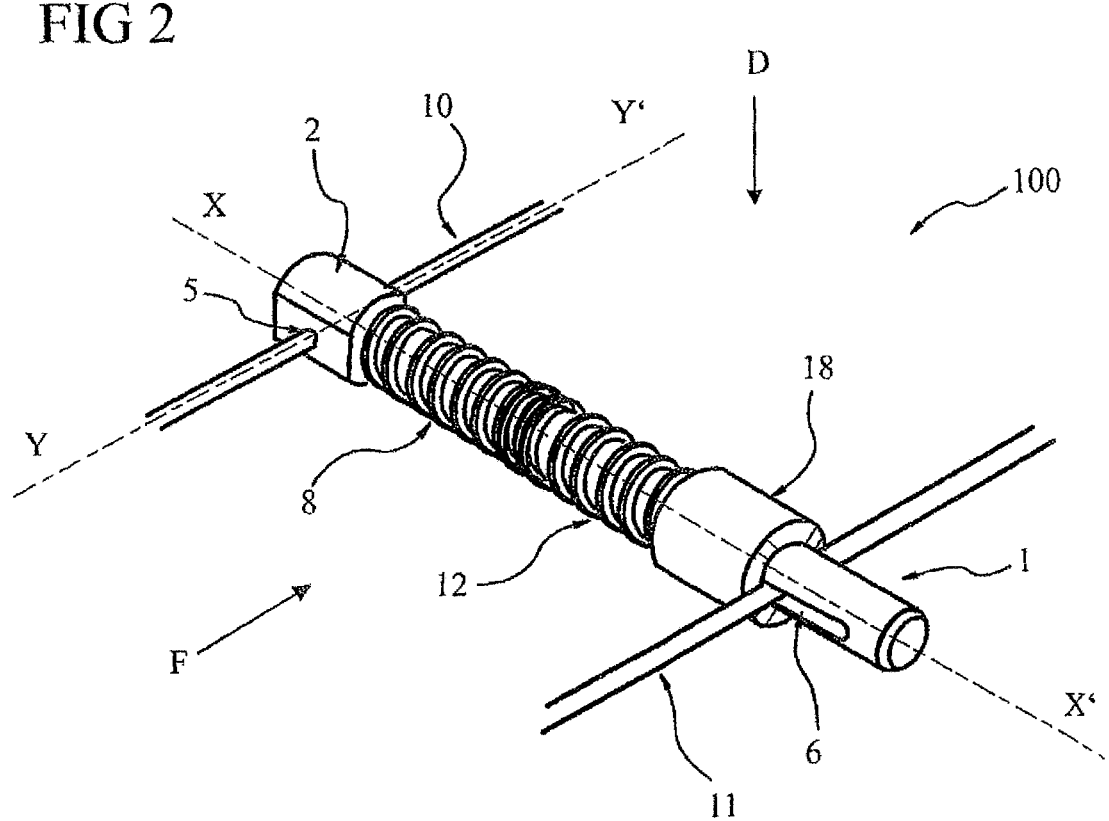
Figure 3:
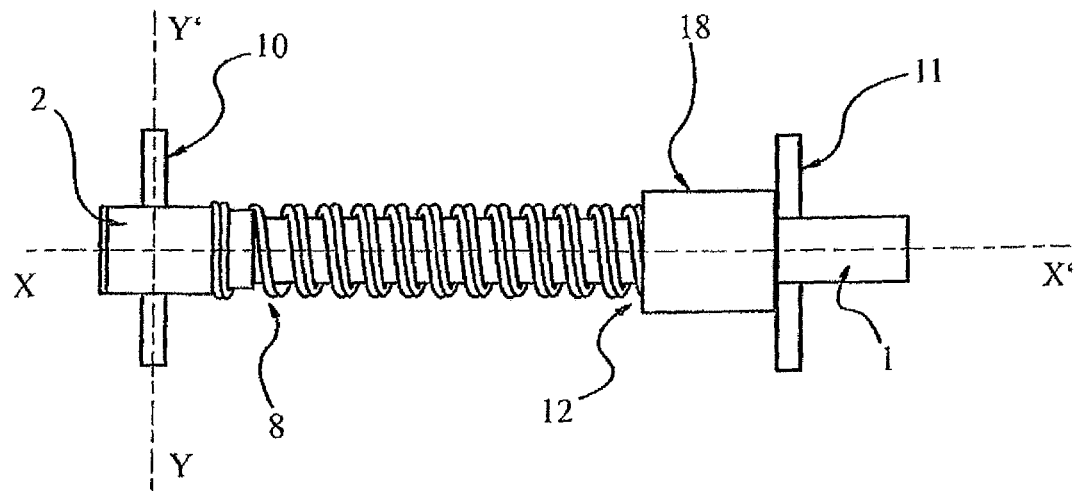
Figure 4:
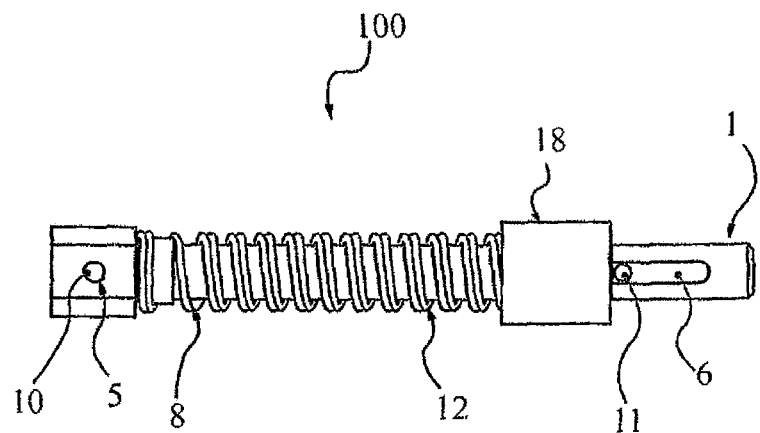

The invention is thus, as illustrated in FIG. 1, in the form of a pair of dynamic external fixation devices (100), arranged on either side of two parts of bone to be consolidated, namely a first portion of bone (O1) located in the proximal portion and a second portion of bone (O2) located in the distal portion. The pair of dynamic external fixation devices (100) is connected by two pins (10, 11), that is, a first pin (10) in the proximal position, and a second pin (11) in a distal position, which cross right through the bone portions (O1, O2) to be consolidated.

In addition, a dynamic external fixation device (100) according to the invention comprises a first body (1), having a longitudinal profile, of the general axis (X, X'), mounted in cooperation with a second body. Each of the two bodies is mounted together with a coil spring (8, 12). The coil springs (8, 12) are mounted nested in opposition, their respective coils being assembled one with the other.

The second spring (12) is nested in rotation in the first spring (8). The second spring (12) is subjected to movements of rotation, compression and expansion, while the first spring (8) is only subjected to compression and expansion movements.

According to the embodiments, the second spring (12) advantageously has a larger coil diameter than the first spring (8). This characteristic allows the rotation of the second spring (12) by a collar (18) rotationally mounted on the latter by a suitable thread, as explained in more detail in the following description.

According to other embodiments, the two springs (8, 12) have the same diameter of the coil, advantageously when the second body, namely a collar (18) is mounted, in combination, at the end, of the distal end of the second spring (8).

Note that adjustment of the traction or distraction of the two bone portions (O1, O2), via the pins (10, 11), is achieved by the rotation of the second spring (12). This rotational movement of the second spring (12) is advantageously generated either alone, or by the rotation of the second body or by the rotation of a collar (18). In distraction, one of the two or both springs (8, 12) undergo(es) advantageously a compression movement, while in tension, these or one of these advantageously undergo(es) an expansion.

Note that the first body (1) comprises a proximal portion (2), in which is arranged at least one proximal bore (5) passing through an axis (Y, Y'), a central portion (3), and a distal portion (4).

According to one embodiment, the first body (1) comprises a proximal bore (5).

According to some embodiments, the first body (1) comprises two proximal bores (5), more preferably three proximal bores (5). These latter are advantageously aligned along one axis parallel to the other axis (X, X').

According to some embodiments, at least the distal portion (4) comprises a longitudinal lumen (6) along the axis (X, X'). The plane passing through the lumen (6) is arranged parallel to the axis (Y, Y') passing through one proximal bore (5), but it could be otherwise, the plane passing through the lumen (6) is arranged perpendicularly to the axis (Y, Y') passing through the proximal bore (5).

It should be noted that the proximal portion (2) of the first body (1) has a more prominent section than that of the central (3) and distal (4) part. The junction of the proximal portion (2) and the central portion (3) forms a first shoulder (7) serving as a compression stop for the first coil spring (8), mounted at least along the central portion (3).

According to one feature, the proximal end of the first spring (8) is engaged in a recess (9), arranged in line with the first shoulder (7). The first spring (8) is thus locked in rotation by the recess (9) and stops against the first shoulder (7) during compression movement.

Figure 5:
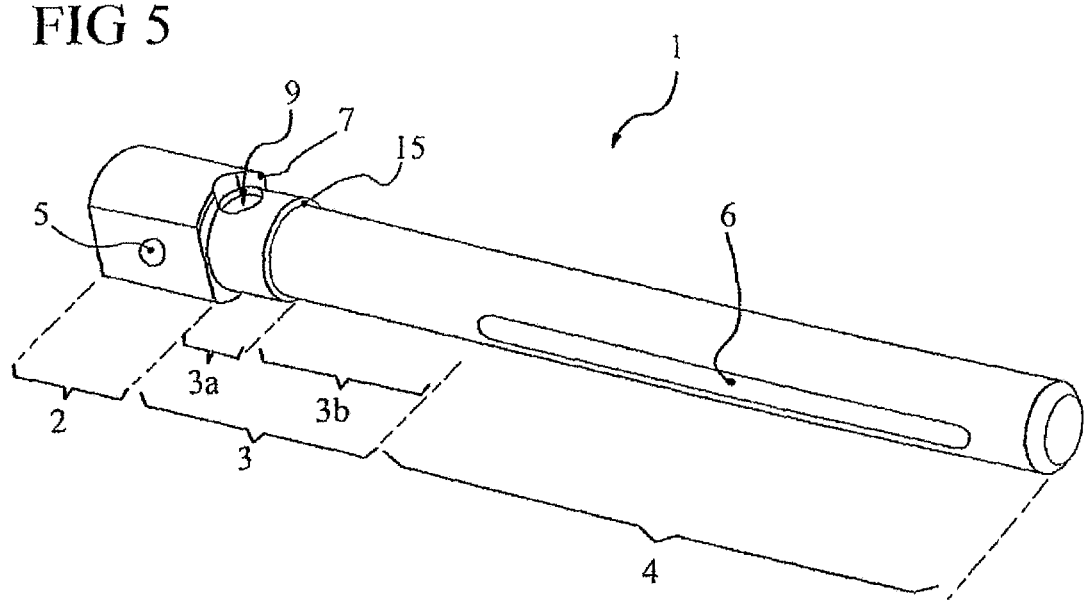

According to another feature, the proximal portion (2) has a truncated cylindrical section. This section, according to one embodiment, as illustrated in FIG. 5, has two parallel sides and two concave-shaped sides in opposing position. This particular configuration allows minimal obstruction when one or both external fastening device(s) (100) is/are placed, for example, between two fingers.

According to an additional feature, the central portion (3) is composed of two parts, namely a first portion (3a) of larger section and a second portion (3b) of a less prominent section. The junction of these latter two parts (3a, 3b) of the central portion (3) forms a second shoulder (15), serving as a stop for the second spring (12), in an extreme distraction position.

According to some embodiments, the second portion (3b) advantageously has a full section in order to limit the size of the lumen (6) arranged at least in the distal portion (4) and thus to limit the displacement of the second pin (11), inserted in the latter.

Additionally, the second body advantageously has a cylindrical section and an internal diameter equal to or substantially greater than the outside diameter of the distal portion (4) of the first body (1), but it could be otherwise, the internal diameter of the second body is equal to or substantially greater than the diameter of the second spring (12).

Figure 6:
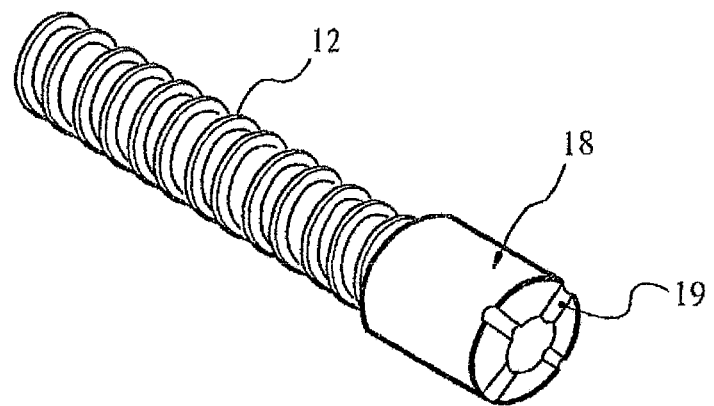

According to one embodiment, as illustrated in FIGS. 2 to 6, the first body (1), as illustrated in more detail in FIG. 5, comprises a longitudinal lumen arranged parallel to the axis (Y, Y') passing through a proximal bore (5). The second pin (11) in the distal portion (4) is arranged in the lumen (6). The second body, as further illustrated in FIG. 6, is a collar (18) in combination with the distal end of the second coil spring (12). The assembly constituted by the collar (18) and the second spring (12) is rotationally mounted on the first body (1). The distal portion of the second body stops against the second pin (11). The second body is thus located between the two pins (10, 11), more precisely limited by the second pin (11) and the proximal portion (2) of the first portion body (1), more precisely limited by the central portion (3) of the latter. Grooves (19) are provided at the distal end of the second body to facilitate engaging and holding the body against the second pin (11).

Figure 7:
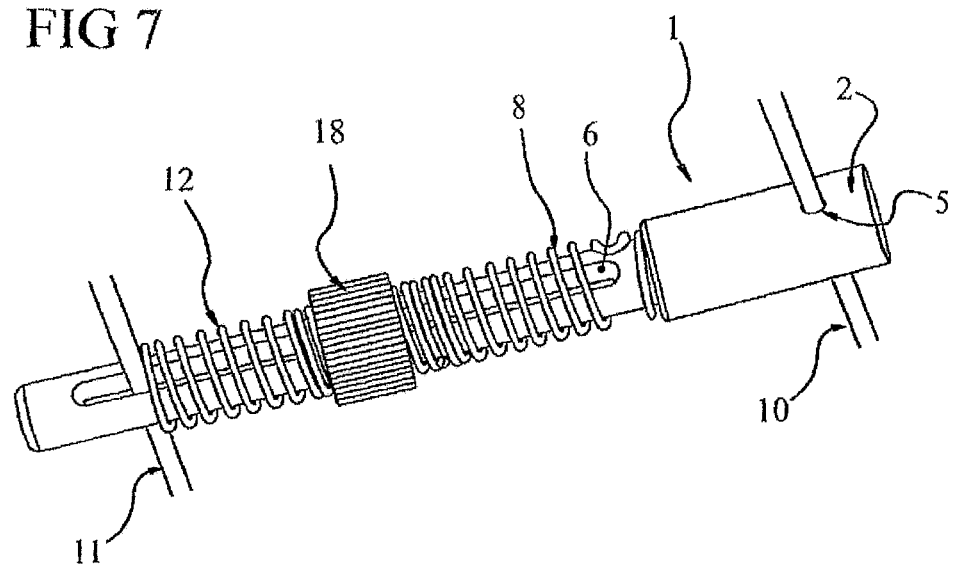
FIG. 7 is a perspective view of a dynamic external fixation device (100) according to another embodiment of the invention.

According to an alternative of the invention, as illustrated in FIG. 7, the first body comprises a lumen (6) arranged parallel to the axis (Y, Y') passing through a proximal bore (5), while the second body is a collar (18) rotationally mounted on the second spring (12). The second body comprises in its inner wall a thread complementary to the coil of the second spring (12). The second spring (12) is further rotationally mounted on the first body (1). The distal portion of the second spring (12) stops against the second pin (11). The second pin (11) in the distal portion (4) is arranged in the lumen (6).

Figure 8:
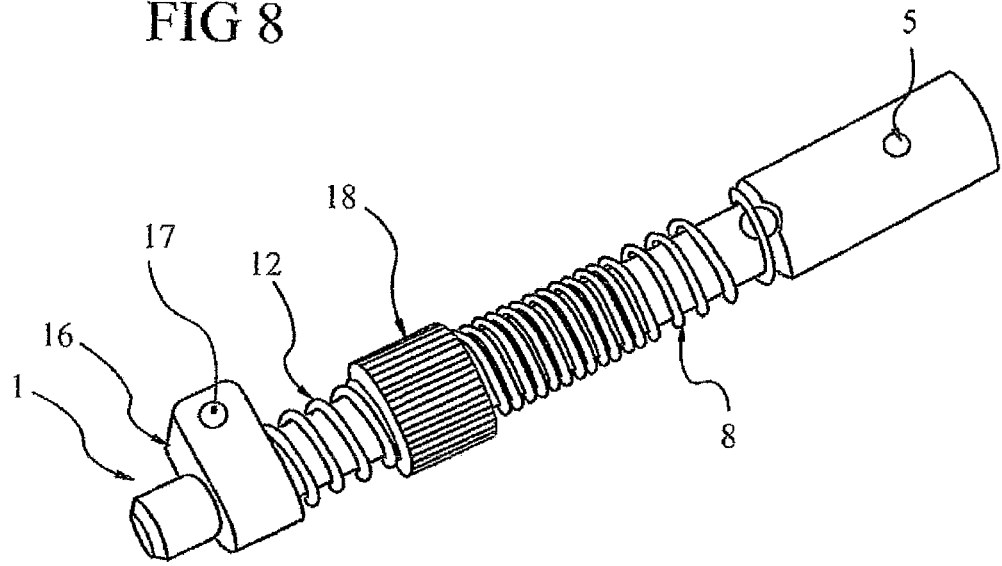
FIGS. 8 to 10 are views of a dynamic external fixation device (100) according to an embodiment of the invention.
Figure 9:
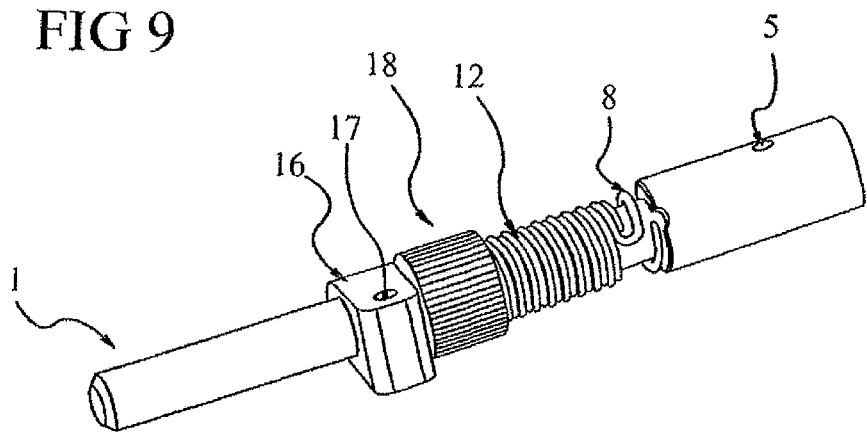
Figure 10:
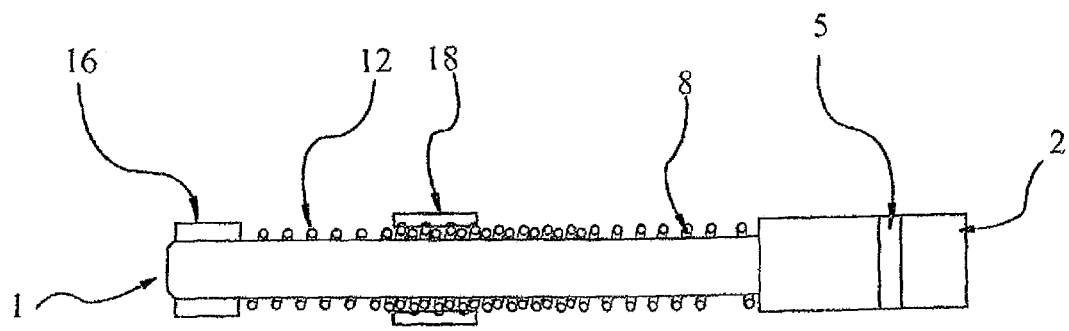

According to one embodiment, as illustrated in FIGS. 8 to 10, the second body is a first collar (16) comprising a distal bore (17) with an axis oriented parallel to the axis (Y, Y') of the proximal bore (5), the second pin (11) being arranged in the bore (17). The second spring (12) is mounted in cooperation with the first collar (16), namely, the distal end of the second spring (12) stops against the proximal portion of the first collar (16), while a second collar (18) is rotationally mounted on the second spring (12). The second collar (18) comprises in its inner wall a thread complementary to the coil of the second spring (12).

According to an alternative of the previous embodiment, the second collar (18) is not rotationally mounted on the second spring (12), but at the end of the latter.

According to another alternative of the preceding embodiment, the external fixing device (100) does not comprise a second collar (18).

Figure 11:
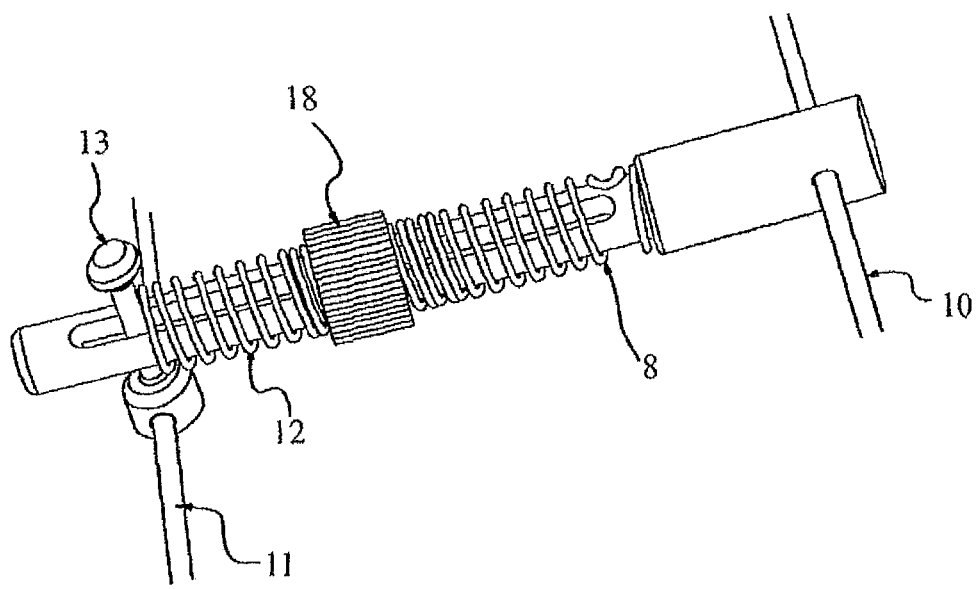
FIGS. 11 and 12 are views of the dynamic external fixation device (100), according to another embodiment of the invention.
Figure 12:
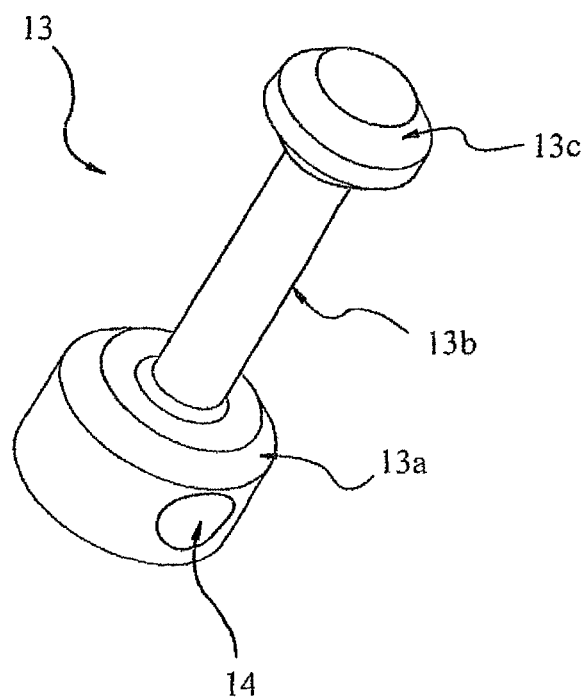

According to another embodiment, as illustrated in FIG. 11, the lumen (6) is arranged perpendicular to the axis (Y, Y') passing through a proximal bore (5). The second body is a pivot (13), comprising a distal bore (14). The pivot (13) is inserted into the lumen (6). This pivot (13) consists of a head (13a) comprising a distal bore (14), a body (13b) cooperating with the lumen (6) and a closure element (13c). It is understood that the second pin (11) is inserted into the distal bore (14) of the head (13a) of the pivot (13), to be arranged parallel to the first pin (10). One collar (18), as shown in more detail in FIG. 6, is in combination with the distal end of the second coil spring (12). The assembly constituted by the collar (18) and the second spring (12) is rotationally mounted on the first body (1). The distal end of the collar (18) stops against the proximal portion of the pivot (13).

According to an alternative of the preceding embodiment, the second collar (18) is not mounted at the end on the second spring (12), but rotationally on the latter.

According to another alternative of the preceding embodiment, the external fixation device (100) does not comprise a second collar (18).

The invention claimed is:

1. A pair of dynamic external fixation devices (100) for the reduction of fractures of bone fragments, said devices (100) adapted to be arranged on either side of a first portion of bone (O1) traversed by a first associated pin (10) in a proximal position and a second portion of bone (O2) traversed by a second associated pin (11) in a distal position, each of the dynamic external fixation devices (100) comprising:
 a first body (1) comprising a longitudinal axis profile (X, X'), said first body comprising at least one proximal bore (5) passing therethrough along a bore axis (Y, Y') and adapted to receive the first associated pin (10);
 a first coil spring, wherein said first body (1) is at least partially inserted into the first coil spring (8);
 a second coil spring, wherein said first spring (8) is nested in the second coil spring (12);
 a second body (13,16,18) with which the second coil spring (12) is engaged, said second body (13, 16, 18) movably engaged with said first body (1), wherein the second body (13, 16, 18) is adapted to engage the second associated pin (11).

2. The pair of dynamic external fixation devices (100) according to claim 1, wherein the first body (1) comprises a lumen (6) arranged longitudinally along the axis (X, X'), said lumen adapted for receiving the second associated pin.

3. The pair of dynamic external fixation devices (100) according to claim 2, wherein the second body comprises a collar (18) in combination with and mounted at a distal end of the second spring (12), wherein a distal end of said collar (18) is adapted to interact with the second associated pin (11) arranged in the lumen (6), wherein the second associated pin is oriented parallel to the bore axis (Y, Y').

4. The pair of dynamic external fixation devices (100) according to claim 3, wherein the first body (1) comprises a proximal portion (2) in which is arranged said at least one proximal through bore (5) for receiving the first associated pin (10), a central portion (3), and a distal portion (4).

5. The pair of dynamic external fixation devices (100) according to claim 2, wherein the first body (1) comprises a proximal portion (2) in which is arranged said at least one proximal through bore (5) for receiving the first associated pin (10), a central portion (3), and a distal portion (4).

6. The pair of dynamic external fixation devices (100) according to claim 1, wherein the first body (1) comprises a lumen (6) arranged longitudinally along the axis (X, X'), and wherein the second body comprises a pivot (13) including: (i) a head (13a) comprising a distal bore (14) adapted to interact with the second associated pin (11), (ii) a pivot body (13b) movably received in the lumen (6) and oriented perpendicularly to the bore axis (Y, Y'), and (iii) a closure element (13c) arranged in opposition to the head (13a).

7. The pair of dynamic external fixation devices (100) according to claim 6, wherein each of the devices (100) comprises a collar (18) in combination with and mounted at a distal end of the second spring (12), while a distal end of said collar (18) interacts with a proximal end of the pivot (13).

8. The pair of dynamic external fixation devices (100) according to claim 6, wherein each of the devices (100) comprises a collar (18) comprising a thread complementary to a coil of the second spring (12), and wherein said collar (18) is mounted rotationally on the second spring (12), while a distal end of the second spring (12) interacts with a proximal end of the pivot (13).

9. The pair of dynamic external fixation devices (100) according to claim 1, wherein the second body comprises a first collar (16) including a distal through bore (17) axially oriented parallel to the bore axis (Y, Y'), wherein said distal through bore is adapted to interact with the second associated pin (11).

10. The pair of dynamic external fixation devices (100) according to claim 9, wherein each of the devices (100) comprises a second collar (18) comprising a thread complementary to a coil of the second spring (12), said second collar (18) rotationally mounted on the second coil spring (12), a distal end of the second spring (12) interacting with a proximal end of the first collar (16).

11. The pair of dynamic external fixation devices (100) according to claim 9, wherein each of the devices (100) comprises a second collar (18) in combination with a distal end of the second spring (12), said second collar (18) mounted at the distal end of the second spring (12), the distal end of said second collar (18) interacting with a proximal end of the first collar (16).

12. The pair of dynamic external fixation devices (100) according to claim 1, wherein the first body (1) comprises a proximal portion (2) in which is arranged said at least one proximal through bore (5), a central portion (3), and a distal portion (4).

13. The pair of dynamic external fixation devices (100) according to claim 12, wherein the proximal portion (2) of the first body has a more prominent section than that of the central portion (3) and distal portion (4), and wherein a junction of the proximal portion (2) and the central portion (3) forms a shoulder (7) serving as a compression stop for the first coil spring (8).

14. The pair of dynamic external fixation devices (100) according to claim 13, wherein a proximal end of the first spring (8) is engaged in a recess (9), arranged in line with the shoulder (7), wherein said first spring (8) is blocked rotationally by the recess (9) and stops against the shoulder (7).

15. The pair of dynamic external fixation devices (100) according to claim 14, wherein the central portion (3) comprises a proximal central portion (3*a*) and a second central portion (3*b*), wherein the proximal central portion (3*a*) is of a more prominent section as compared to said second central portion (3*b*), and wherein a junction of the proximal central portion and second central portion (3*a*, 3*b*) forms a second shoulder (15) serving as a stop at a proximal end of the second spring (12) in an extreme distraction position.

16. The pair of dynamic external fixation devices (100) according to claim 15, wherein the proximal portion (2) of the first body (1) comprises a truncated cylindrical section including a section comprising two parallel sides.

17. The pair of dynamic external fixation devices (100) according to claim 16, wherein a coil diameter of the second spring (12) is greater than a coil diameter of the first spring (8).

18. A dynamic external fixation device for the reduction of bone fractures, the device comprising:
   a first body having a longitudinal axis, the first body comprising a proximal bore extending therethrough along a proximal bore axis and adapted to receive a first associated pin;
   a first coil spring mounted on the first body;
   a second coil spring nested in the first coil spring;
   a second body engaged with the second coil spring, said second body movably engaged with said first body, wherein the second body or the second spring is adapted to engage a second associated pin;
   wherein the first body comprises a lumen extending longitudinally along the longitudinal axis, wherein the lumen is adapted for passage of the second associated pin therethrough along an axis parallel to the proximal bore axis, said device further comprising a collar mounted at a distal end of the second spring such that said collar is adapted to engage the second associated pin.

19. A pair of dynamic external fixation devices (100) for the reduction of fractures of associated bone fragments, said devices (100) adapted for being arranged on either side of an associated first portion of bone (O1) traversed by a first associated pin (10) in a proximal position and an associated second portion of bone (O2) traversed by a second associated pin (11) in a distal position, each of the dynamic external fixation devices (100) comprising a first body (1) including a longitudinal axis profile (X, X') and including at least one proximal bore (5) passing through an axis (Y, Y') adapted to receive the first associated pin (10), said first body (1) being inserted in a first coil spring (8), wherein said first spring (8) is nested in a second coil spring (12), and wherein the second coil spring is engaged with a second body (13, 16, 18), said second body is fitted around or inserted in said first body (1), and the second body (13, 16, 18) mounted in abutment against the second spring (12) and adapted to engage the second associated pin (11).

* * * * *